(12) United States Patent
Stefan et al.

(10) Patent No.: US 10,537,231 B2
(45) Date of Patent: Jan. 21, 2020

(54) ENDOSCOPIC INSTRUMENT

(71) Applicant: Karl Storz SE & Co. KG, Tuttlingen (DE)

(72) Inventors: Jochen Stefan, Wald (DE); Annika Müller, Geislingen (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 937 days.

(21) Appl. No.: 14/604,027

(22) Filed: Jan. 23, 2015

(65) Prior Publication Data

US 2015/0208903 A1 Jul. 30, 2015

(30) Foreign Application Priority Data

Jan. 24, 2014 (DE) ........................ 10 2014 100 840

(51) Int. Cl.
*A61B 1/005* (2006.01)
*A61B 1/008* (2006.01)
(Continued)

(52) U.S. Cl.
CPC ............ *A61B 1/0055* (2013.01); *A61B 1/008* (2013.01); *A61B 1/0057* (2013.01);
(Continued)

(58) Field of Classification Search
CPC ..... A61B 1/005; A61B 1/0051; A61B 1/0055; A61B 1/0057; A61B 1/008; A61B 1/00071; A61B 1/00078; A61B 1/00098; A61B 1/00105; A61B 1/00128; A61B 1/01; A61M 25/0021; A61M 25/0043; A61M 25/0054; A61M 25/0141; A61M 25/0144;
(Continued)

(56) References Cited

U.S. PATENT DOCUMENTS

| 7,658,305 B2 * | 2/2010 | Voegele ........... A61B 17/00491 222/387 |
| 2005/0096694 A1 | 5/2005 | Lee |
| 2007/0152014 A1 | 7/2007 | Gillum et al. |

FOREIGN PATENT DOCUMENTS

| DE | 102007038386 A1 | 3/2008 |
| EP | 1915950 A1 | 4/2008 |
| WO | 2013116692 A1 | 8/2013 |

OTHER PUBLICATIONS

European Search Report Application No. EP 15 15 0628 Completed: Jun. 9, 2015; dated Jun. 18, 2015 7 pages.

* cited by examiner

*Primary Examiner* — Shefali D Patel
(74) *Attorney, Agent, or Firm* — Whitmyer IP Group LLC (57) ABSTRACT

An endoscopic instrument including first, second and third portions, a first main hinge with a first main-hinge part, a further first main-hinge part and a first sub-hinge, a second main hinge with a second main-hinge part, a further second main-hinge part and a second sub-hinge, and a rigid main pressure rod. The first and second portions are connected via the first main hinge, such that the first and second portions can be angled. The first and third portions are connected via the second main hinge such that the first and third portions can be angled. The main pressure rod is coupled to the first and second sub-hinges, so that displacement of the first main hinge by angling the second portion relative to the first portion transmits a force, via the main pressure rod, to the second main hinge and causes an angling of the third portion relative to the first portion.

15 Claims, 6 Drawing Sheets

(51) Int. Cl.
*A61B 1/00* (2006.01)
*A61M 25/01* (2006.01)
(52) U.S. Cl.
CPC ...... *A61B 1/00098* (2013.01); *A61B 1/00105* (2013.01); *A61M 25/0144* (2013.01)
(58) Field of Classification Search
CPC .. A61M 2025/0161; A61M 2025/0063; A61M 2025/0175
See application file for complete search history.

ENDOSCOPIC INSTRUMENT

FIELD OF THE INVENTION

The present disclosure relates to an endoscopic instrument having a first portion, which has a first longitudinal extent, and having a second portion and a third portion.

BACKGROUND OF THE INVENTION

Displacement of the distal end of rigid endoscopic instruments is possible in a particularly straightforward and intuitive manner. The reason for this is that any movement at the proximal end results directly in a predictable displacement of the distal end. Also, force is transmitted directly from the proximal end to the distal end.

Since rigid endoscopic instruments are introduced into the body usually through a natural or artificially created channel, displacement of the distal end, however, is possible only to a limited extent. As the length of the introduction channel increases, the possible movement space for the distal end decreases more and more. It is therefore desired that the distal end may be displaced with a greater amount of freedom, even if the endoscopic instrument as a whole can be moved only to a very limited extent.

There is therefore a multiplicity of solutions for flexible endoscopes. However, sometimes the distal end can be controlled only inaccurately and not particularly intuitively. In addition, direct feedback from the distal end to the proximal operating element is often lacking. Finally, providing a sufficient transmission of force from the proximal end to the distal end of the endoscopic instrument may also be very complex.

SUMMARY OF THE INVENTION

It is therefore an object to provide an endoscopic instrument which can be angled, in one exemplary embodiment a number of times, at the distal end. It is a further object to have a simple transmission of force from the proximal end to the distal end and to have a good force-feedback from the distal end to the proximal end.

There is provided an endoscopic instrument comprising a first portion, which has a first longitudinal extent, a second portion and a third portion, a first main hinge, which has a first main-hinge part, a further first main-hinge part and a first sub-hinge, a second main hinge, which has a second main-hinge part, a further second main-hinge part and a second sub-hinge, and a rigid main pressure rod, which extends along the first longitudinal extent, wherein the first portion and the second portion are connected to one another via the first main hinge, such that they can be angled, wherein the first portion and the third portion are connected to one another via the second main hinge such that they can be angled, and wherein the main pressure rod is coupled to the first sub-hinge and the second sub-hinge, so that displacement of the first main hinge by angling the second portion relative to the first portion transmits a force, via the main pressure rod, to the second main hinge and causes there an angling of the third portion relative to the first portion.

This construction allows to achieve an angling at the second main hinge by angling at the first main hinge. Force may be transmitted in one exemplary embodiment in a purely mechanical manner, in particular without being assisted by a motor.

The main pressure rod is of rigid design, and therefore a force which is transmitted to the main pressure rod by angling the second portion is transmitted directly to the second main hinge. This may achieve particularly reliable functioning.

Arranging the first sub-hinge on the first main hinge and the second sub-hinge on the second main hinge allows, for some exemplary embodiments, for the angling at the first main hinge to be transferred to the angling at the second main hinge. To give a better understanding of this aspect, for orientation purposes, a first center axis of the first portion is used, the first center axis extending through a first center point of the first main hinge and through a second center point of the second main hinge. These center points here should each be understood in particular as the point about which the respective main hinge pivots.

If the first sub-hinge is spaced apart from the first center axis by a smaller distance than the second sub-hinge, then angling at the first main hinge about a first angle generates angling at the second main hinge about a second angle, which is smaller than the first angle. If the first sub-hinge is spaced apart from the first center axis by a distance which is larger than the distance between the second sub-hinge and the first center axis, then angling of the first main hinge about a first angle results in angling at the second main hinge by a second angle, which is larger than the first angle.

It is possible to select the desired ratio between the first and second angles in dependence on a first maximum angle range, over which the first main hinge is to be angled, and a desired second maximum angle range, over which the second main hinge is to be angled. In the same way, it is also possible for a first torque at the first main hinge to be converted at a ratio to a second torque at the second main hinge.

A refinement, however, in particular provides that the distance between the first sub-hinge and the first center axis is at least approximately equal to the distance between the second sub-hinge and the first center axis. Then, deflection about a first angle at the first main hinge is equal to deflection about a second angle at the second main hinge. This allows particularly intuitive operation, in particular because displacement of the second portion relative to the first portion causes a displacement of the third portion relative to the first portion with the same torque and the same magnitude. It is possible, in addition, to realize a further exemplary refinement in which the main pressure rod runs at least approximately parallel to the first center axis.

It should be noted that, in case of certain exemplary embodiments, at least parts of the main pressure rod do not run parallel to the first center axis. According to an exemplary embodiment, the first sub-hinge is arranged beneath the second sub-hinge at the same distance from the first center axis, but the radial position of the first sub-hinge is located diametrically opposite the radial position of the second sub-hinge. In case of this embodiment, this may mean, in particular, that the main pressure rod crosses over the first center axis. Such an embodiment is considered if it is desired for deflection at the first main hinge in a certain direction, e.g. to the left, to result in movement at the second main hinge in the same direction.

In comparison: if the main pressure rod is guided parallel to the first center axis, angling of the first main hinge in a certain direction results in angling at the second main hinge in the opposite direction. It is also possible for a plurality of main pressure rods to cross over the center axis. All that must then be ensured is for the crossover points with the first center axis to be distributed along the first center axis and to be spaced apart sufficiently from one another.

It should be pointed out that the term "pressure", in respect of the present disclosure, should contain the meaning of a positive pressure, that is to say "pushing action", since one of the particular aspects of the present disclosure is considered to be the transmission of a pushing action from the proximal end to the distal end of the endoscopic instrument. This does not preclude, however, the term "pressure" also relating to a negative pressure, that is to say a "pulling action". Rather, it is the case that the rigidity of the main pressure rod allows the transmission both of a pushing action and of a pulling action.

Suitable coupling of the main pressure rod to the first sub-hinge and the second sub-hinge allows for the main pressure rod to transmit both a pushing action and a pulling action between the first sub-hinge and the second sub-hinge. If the main pressure rod is connected to the first sub-hinge and/or the second sub-hinge such that there is freewheeling either in the pushing direction or in the pulling direction, the coupling may also be configured such that only a pushing action or only a pulling action is transmitted. However, it may be preferred that the main pressure rod is coupled to the first sub-hinge and the second sub-hinge such that both a pushing action and a pulling action is transmitted from the first sub-hinge to the second sub-hinge. According to an exemplary embodiment, the first portion has a first cavity along the first longitudinal extent.

It should also be noted that the use of the term "longitudinal extent" serves merely to introduce a reference system. A longitudinal extent of the endoscopic instrument should be understood here in particular as the extent from the proximal end to the distal end of the endoscopic instrument. In the rest state of the endoscopic instrument, that is to say in the non-deflected state, the longitudinal extents of the individual portions, for orientation purposes, are understood as being at least approximately parallel to the longitudinal extent of the endoscopic instrument or coincide at least approximately with the longitudinal extent of the endoscopic instrument.

The term "hinge", within the context of the description, should cover both multi-part hinges, e.g. a ball-and-socket hinge, a rotary hinge or a turning and sliding hinge, and single-part hinges, e.g. solid hinges. In case of a single-part hinge, the first hinge part is then a first portion of the hinge and the further hinge part is a second portion of the hinge.

According to a refinement, the first main-hinge part and the second main-hinge part are arranged on the first portion, the further first main-hinge part is arranged on the second portion and the further second main-hinge part is arranged on the third portion.

This refinement allows a construction of straightforward design.

According to another refinement, the first main-hinge part is designed at least in the form of a portion of a socket and the further first main-hinge part is designed at least in the form of a portion of a ball.

This refinement allows a particularly large amount of freedom in angling the second portion and/or the third portion in a number of directions.

As an alternative, or in addition, in case of another refinement, the second main-hinge part is designed at least in the form of a portion of a socket and the further second main-hinge part is designed at least in the form of a portion of a ball. The same explanations as were given for the first main-hinge part apply correspondingly.

According to another refinement, the first sub-hinge has a first sub-hinge part and a further first sub-hinge part, wherein the first sub-hinge part is formed on the further first main-hinge part, and wherein the further first sub-hinge part is formed on the main pressure rod.

This refinement may be interesting in design terms because the further first main-hinge part, rather than being just part of the first main hinge, has the first sub-hinge part at the same time. The first sub-hinge part can be formed on the further first main-hinge part, according to an exemplary embodiment, by appropriate shaping of the further first main-hinge part. The first sub-hinge part here is formed, according to some exemplary embodiments, in one piece, from the same material or material mix, with the further first main-hinge part. Correspondingly, according to some exemplary embodiments, the further first sub-hinge part is formed in one piece with the main pressure rod or a distal end of the main pressure rod. The further first sub-hinge part here is formed on the main pressure rod, according to an exemplary embodiment, in the form of a ball.

As an alternative, or in addition, the second sub-hinge has a second sub-hinge part and a further second sub-hinge part, wherein the second sub-hinge part is formed on the further second main-hinge part, and wherein the further second sub-hinge part is formed on the main pressure rod. The same explanations as were given for the first sub-hinge apply correspondingly.

According to another refinement, the first sub-hinge part is designed at least in the form of a portion of a socket and the further first sub-hinge part is designed at least in the form of a portion of a ball.

This refinement may make it possible for the first sub-hinge part to be realized in a reliable and space-saving manner.

As an alternative, or in addition, in case of another refinement, the second sub-hinge part is designed at least in the form of a portion of a socket and the further second sub-hinge part is designed at least in the form of a portion of a ball. The same explanations as were given for the first sub-hinge part apply correspondingly.

According to another refinement, three first sub-hinges are arranged on the first main hinge.

This refinement may transmit the pivoting of the second portion to the third portion in a particularly precise manner. In this context, according to an exemplary embodiment, there are also three second sub-hinges arranged on the second main hinge. According to an exemplary embodiment, each of the first sub-hinges is connected to a corresponding one of the second sub-hinges, according to another exemplary embodiment, via additional main pressure rods. According to an exemplary embodiment, the three main pressure rods run parallel to one another, in particular in each case parallel to the first center axis. In case of other refinements, each of the main hinges has precisely two sub-hinges. In case of further refinements, the main hinges each have four or more sub-hinges.

According to another refinement, the first sub-hinges are spaced apart relative to one another by a distance of between 45° and 120°, to be precise in relation to the aforementioned first center axis of the first portion, the first center axis running through a first center point of the first main hinge and through a second center point of the second main hinge. In case of a further refinement, the first sub-hinges are spaced apart relative to one another by a distance of at least approximately 120°.

As an alternative, or in addition to this, three second sub-hinges of the second main hinge are spaced apart relative to one another by a distance of between 45° and 120°, to be precise in relation to the aforementioned first center axis. In the same way, what has been said in relation to the first sub-hinges applies correspondingly.

According to another refinement, the further first main-hinge part has a first inner hinge, which is arranged in the interior of the further first main-hinge part and is arranged such that it can be pivoted relative to the further first main-hinge part, wherein the second portion has a second longitudinal extent and a second cavity along the second longitudinal extent.

This refinement may be interesting because the first inner hinge may be used to transmit a further actuating movement which may be independent of a displacement of the further first main-hinge part.

As an alternative, or in addition to this, in case of another refinement, the further second main-hinge part has a second inner hinge, which is arranged in the interior of the further second main-hinge part and is arranged such that it can be pivoted relative to the further second main-hinge part. If a first inner hinge and a second inner hinge are present, displacement of the first inner hinge can be transmitted to the second inner hinge, and vice versa.

According to another refinement, the first inner hinge has a first inner-hinge part and a further first inner-hinge part, wherein the at least in particular first inner-hinge part is designed at least in particular in the form of a portion of a socket and the further first inner-hinge part is designed in particular at least in the form of a portion of a ball, the design being in particular in the form of a socket ring.

This refinement allows a particularly reliable and flexible transmission of force. As an alternative, or in addition, the second inner hinge, in case of an exemplary embodiment, has a second inner-hinge part and a further second inner-hinge part, wherein the second inner-hinge part is designed at least in the form of a portion of a socket and the further second inner-hinge part is designed at least in the form of a portion of a ball. The same things as have been said in relation to the first inner hinge apply correspondingly.

According to another refinement, the first inner-hinge part is formed on the further first main-hinge part.

This refinement may be interesting in design terms because the further first main-hinge part, rather than being just part of the first main hinge, has the first inner-hinge part at the same time. The first inner-hinge part can be formed on the further first main-hinge part, according to an exemplary embodiment, by appropriate shaping of the further first main-hinge part. According to an some exemplary embodiments, the first inner-hinge part here is formed in one piece, from the same material or material mix, with the further first main-hinge part.

According to another refinement, the further first inner-hinge part has a first primary hinge with a first primary-hinge part and a further first primary-hinge part, wherein the first primary-hinge part is formed on the further first inner-hinge part.

This refinement may easily make it possible to transmit an actuating movement to the first inner hinge.

As an alternative or in addition to this, the further second inner-hinge part, in case of a refinement, has a second primary hinge with a second primary-hinge part and a further second primary-hinge part, wherein the second primary-hinge part is formed on the further second inner-hinge part. The same things as have been said in relation to the further first inner-hinge part apply correspondingly.

According to another refinement, the endoscopic instrument also has a rigid secondary pressure rod, which extends along the first longitudinal extent, wherein in particular the first primary-hinge part is formed on the secondary pressure rod.

This refinement may allow particularly reliable transmission of force.

As an alternative, or in addition to this, in case of a further refinement, the further second primary-hinge part is formed on the secondary pressure rod.

According to another refinement, the endoscopic instrument has a rigid lateral pressure rod, which extends along the second longitudinal extent, wherein the further first inner-hinge part has a first secondary hinge with a first secondary-hinge part and a further first secondary-hinge part, wherein the first secondary-hinge part is formed on the further first inner-hinge part and the further first secondary-hinge part is formed on the first lateral pressure rod.

This refinement may make it possible for the further first inner-hinge part to absorb a force which is transmitted along the first portion, and to transmit this force into the second portion via the first lateral pressure rod.

As an alternative, or in addition to this, the endoscopic instrument, in case of a further refinement, has a second rigid lateral pressure rod, which extends along a third cavity along a third longitudinal extent of the third portion, wherein the further second inner-hinge part has a second secondary hinge with a second secondary-hinge part and a further second secondary-hinge part, wherein the second secondary-hinge part is formed on the further second inner-hinge part and the further second secondary-hinge part is formed on the second lateral pressure rod. The same things as have been said in relation to the refinement with the first rigid lateral pressure rod apply correspondingly.

According to another refinement, the first inner-hinge part has three first primary hinges and three first secondary hinges.

This refinement may allow particularly precise transmission of a movement via the first primary hinges and first secondary hinges. According to an exemplary embodiment, the three first primary hinges are offset with respect to one another in each case by an angle of at least approximately 120° in relation to the first center axis and the three first secondary hinges are offset with respect to one another in each case by at least approximately 120° in relation to the first center axis. It is thus then the case that in each case a first primary hinge is adjacent to two first secondary hinges by in each case approximately 60°, and vice versa, in each case in relation to the first center axis.

As an alternative, or in addition to this, in case of a refinement, the further second inner-hinge part has three second primary hinges and three second secondary hinges. In the same way, what has been said in relation to the further first inner-hinge part applies correspondingly.

According to another refinement, the first portion, at a location along the first longitudinal extent, is divided into a first portion part and a second portion part, and the first portion part and the second portion part are connected by a connecting element such that it is possible to adjust a distance between the first and the second portion parts.

This refinement may simplify production. In particular it is possible for the distance between the first main hinge and the second main hinge to be adjusted very precisely.

Of course, the features which have been mentioned above and those which are yet to be explained herein below can be used not just in the combination specified in each case, but also in other combinations or alone, without departing from the scope of the present disclosure.

BRIEF DESCRIPTION OF THE DRAWINGS

Exemplary embodiments will be explained in more detail in the following description and are illustrated in the drawing, in which.

DETAILED DESCRIPTION OF THE INVENTION

Figure 1:
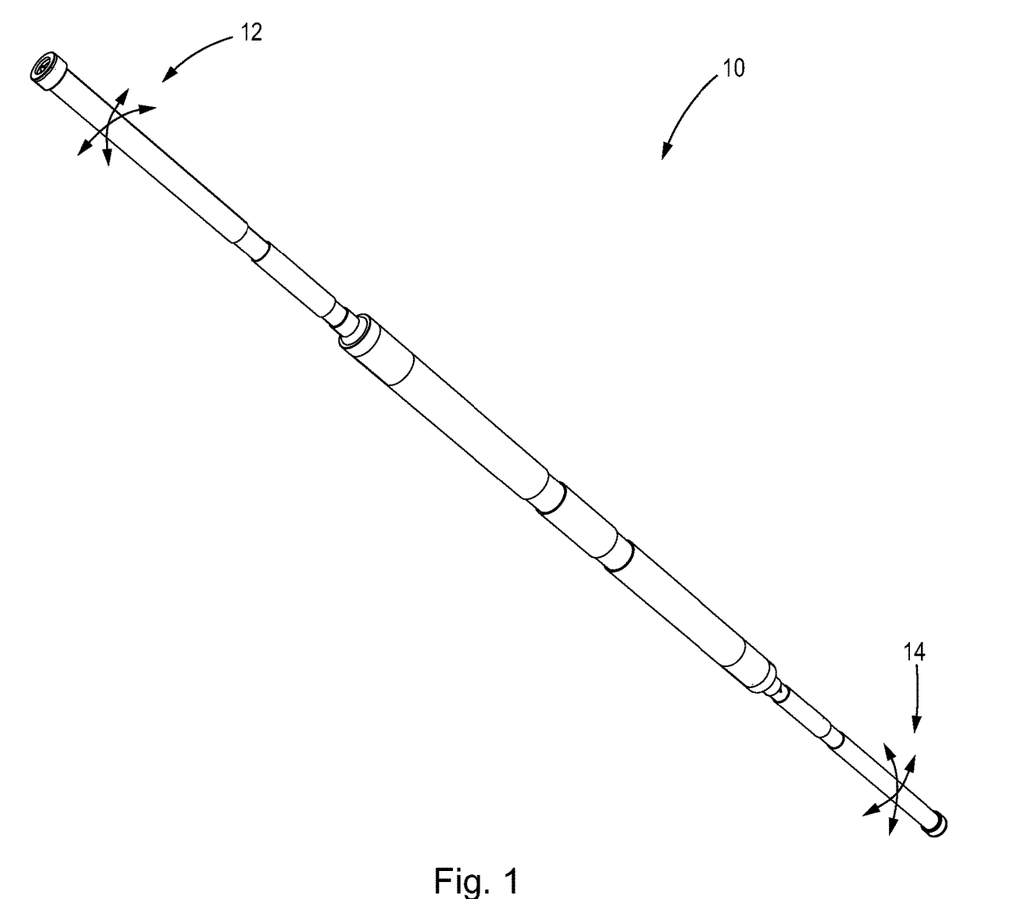
FIG. 1 shows a perspective illustration of a first embodiment of an endoscopic instrument.

FIG. 1 shows a perspective illustration of an endoscopic instrument 10. The double arrows at the proximal end 12 and at the distal end 14 symbolize that displacement at the proximal end 12 may give rise to displacement at the distal end 14.

It should be pointed out that the designations used thus far and hereinbelow apply to all figures and all embodiments, even if the designations are not shown in all the figures and it is also the case that not all the figures refer to all the designations.

Figure 2:
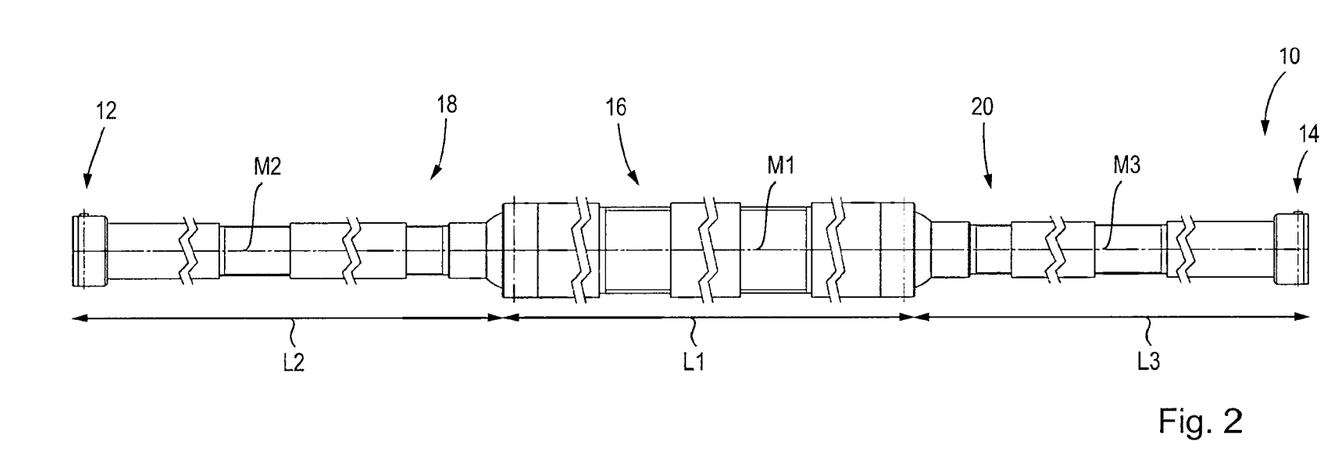
FIG. 2 shows the side view of the endoscopic instrument according to FIG. 1.

FIG. 2 shows a side view of the endoscopic instrument 10 according to FIG. 1. The instrument 10 has a first portion 16 with a first longitudinal extent L1 and a center axis M1, a second portion 18 with a second longitudinal extent L2 and a second center axis M2, and a third portion 20 with a third longitudinal extent L3 and a third center axis M3.

Figure 3:
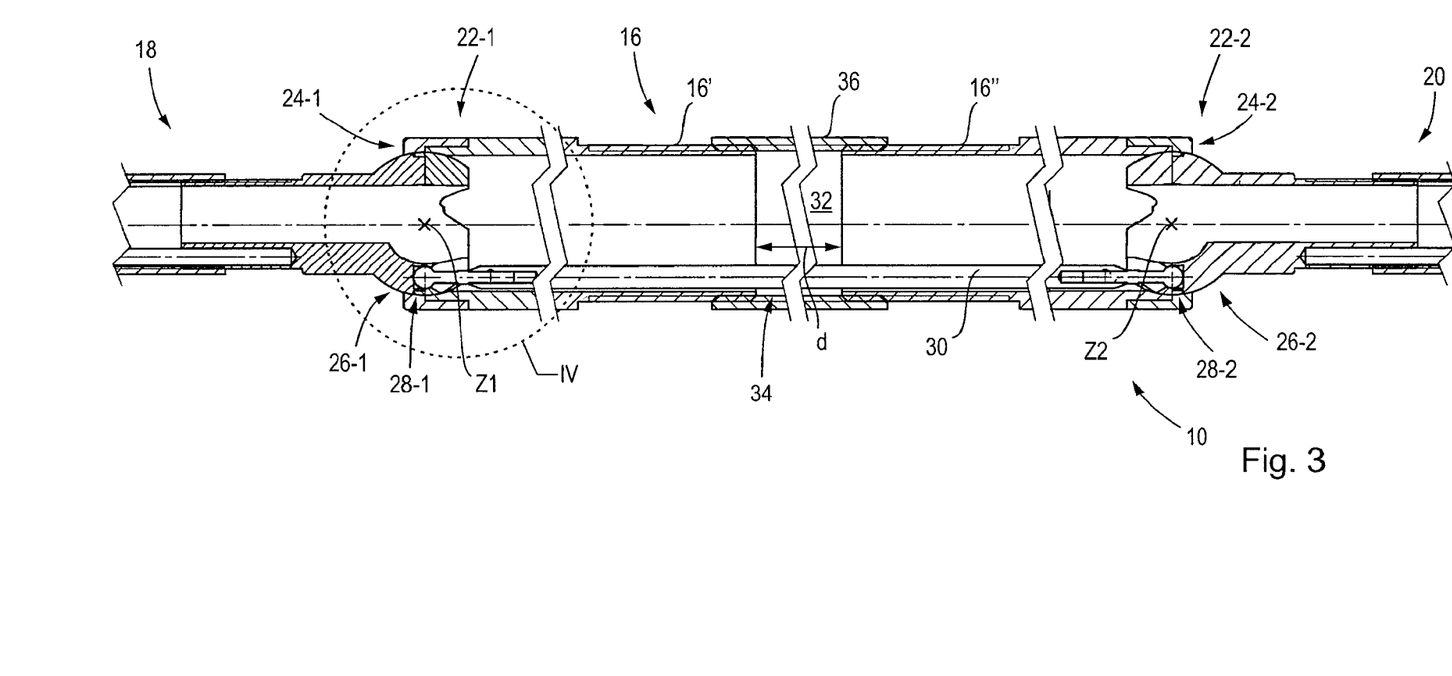
FIG. 3 shows a sectional view of the endoscopic instrument according to FIG. 1.

FIG. 3 shows a sectional illustration of the endoscopic instrument 10 according to FIG. 2, wherein the second portion 18 and the third portion 20 are illustrated only in part. The instrument 10 has a first main hinge 22-1, which has a first main-hinge part 24-1, a further first main-hinge part 26-1 and a first sub-hinge 28-1. The instrument 10 also has a second main hinge 22-2, which has a second main-hinge part 24-2, a further second main-hinge part 26-2 and a second sub-hinge 28-2.

The instrument 10 has a rigid main pressure rod 30, which extends along the first longitudinal extent L1 and parallel to the first center axis M1. The first portion 16 and the second portion 18 are connected to one another such that they can be angled via the first main hinge 22-1. The first portion 16 and the third portion 20 are connected to one another such that they can be angled via the second main hinge 22-2.

The main pressure rod 30 is coupled to the first sub-hinge 28-1 and the second sub-hinge 28-2, and therefore displacement of the first main hinge 22-1 by virtue of the second portion 18 being angled relative to the first portion 16 transmits a force, via the main pressure rod 30, to the second main hinge 22-2 and gives rise there to the third portion 20 being angled relative to the first portion 16.

In case of the embodiment shown, the further first main-hinge part 26-1 and the further second main-hinge part 26-2, during production, each have two parts, of which the separating line runs in each case at least approximately perpendicularly to the first center axis M1 and through the first center point Z1 and the second center point Z2, respectively. The ends of the main pressure rod 30 also each have two parts during production. It is thus possible for the part with the ball to be positioned between the parts of the further first main-hinge part 26-1 and of the further second main-hinge part 26-2, for the parts to be joined together and for the part with the ball to be connected to the central part of the main pressure rod 30.

The sectional illustration shows that the first portion 16 has a first cavity 32, which extends along the first longitudinal extent L1. It is also the case in this embodiment that the first portion 16, at a location 34 along the first longitudinal extent L1, is divided into a first portion part 16' and a second portion part 16". The first portion part 16' and the second portion part 16" are connected to one another by a connecting element 36 such that it is possible to adjust a distance d between the first and the second portion parts 16', 16". It is illustrated schematically that the connecting element 36 here is designed in the form of a sleeve with a right-hand/left-hand thread, which interacts with corresponding threads on the first and second portion parts 16', 16".

Figure 4:
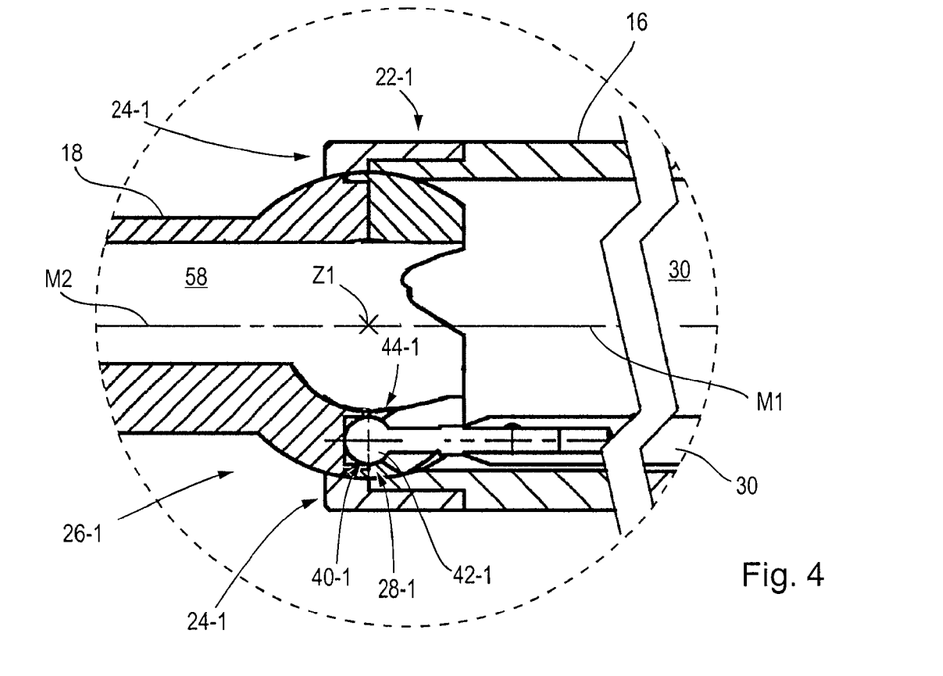
FIG. 4 shows an enlargement of a detail from FIG. 3.

FIG. 4 shows an enlargement of a detail of FIG. 3. The first main hinge 22-1 should be explained with reference to this figure. The explanations relating to the construction of the first main hinge 22-1 also apply correspondingly to the second main hinge 22-2.

As already explained, the first main hinge 22-1 has a first main-hinge part 24-1, a further first main-hinge part 26-1 and a first sub-hinge 28-1. The first main-hinge part 24-1 and the second main-hinge part 24-2 are arranged on the first portion 16. The further first main-hinge part 26-1 is arranged on the second portion 18. Correspondingly, in a manner not shown here, the further second main-hinge part 26-2 is arranged on the third portion 20.

The first main-hinge part 24-1 is designed at least in the form of a portion of a socket. The further first main-hinge part 26-1 is designed at least in the form of a portion of a ball. This embodiment allows the second portion 18 to be angled relative to the first portion 16 in all directions. The further first main-hinge part 26-1, however, cannot be displaced along the first longitudinal extent L1. In other words, a first center point Z1 of the first main hinge 22-1 remains stationary, even along the first longitudinal direction L1, during displacement of the second portion 18.

The first sub-hinge 28-1 has a first sub-hinge part 40-1 and a further first sub-hinge part 42-1. In case of the embodiment shown here, the first sub-hinge part 40-1 is formed on the further first main-hinge part 26-1. The further first sub-hinge part 42-1 is formed on the main pressure rod 30.

In case of this embodiment, the first sub-hinge part 40-1 is designed at least in the form of a portion of a socket and the further first sub-hinge part 42-1 is designed at least in the form of a portion of a ball. The first sub-hinge part 40-1 is formed with an undercut 44-1, and therefore the main pressure rod 30 can subject the further first main-hinge part 26-1 both to positive pressure and to negative pressure.

In case of the embodiment shown here, three first sub-hinges 28-1 are arranged on the first main hinge 22-1, the first sub-hinges being designed like the first sub-hinge 28-1 shown in FIG. 4 and being arranged around the second center axis M2 at various locations of the further first main hinge 26-1.

Figure 5:
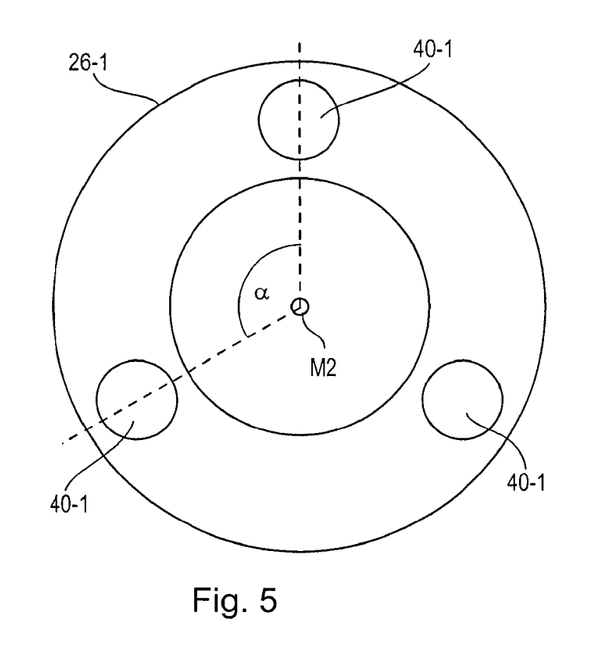
FIG. 5 shows a simplified illustration of a plan view of an end side of the further first main-hinge part.

FIG. 5 depicts the arrangement selected here with the first sub-hinges 28-1, in this case only the first sub-hinge parts 40-1 are illustrated schematically, spaced apart relative to one another by a distance α of 120°, to be precise in relation to the second center axis M2 or to the first center axis M1.

Figure 6:
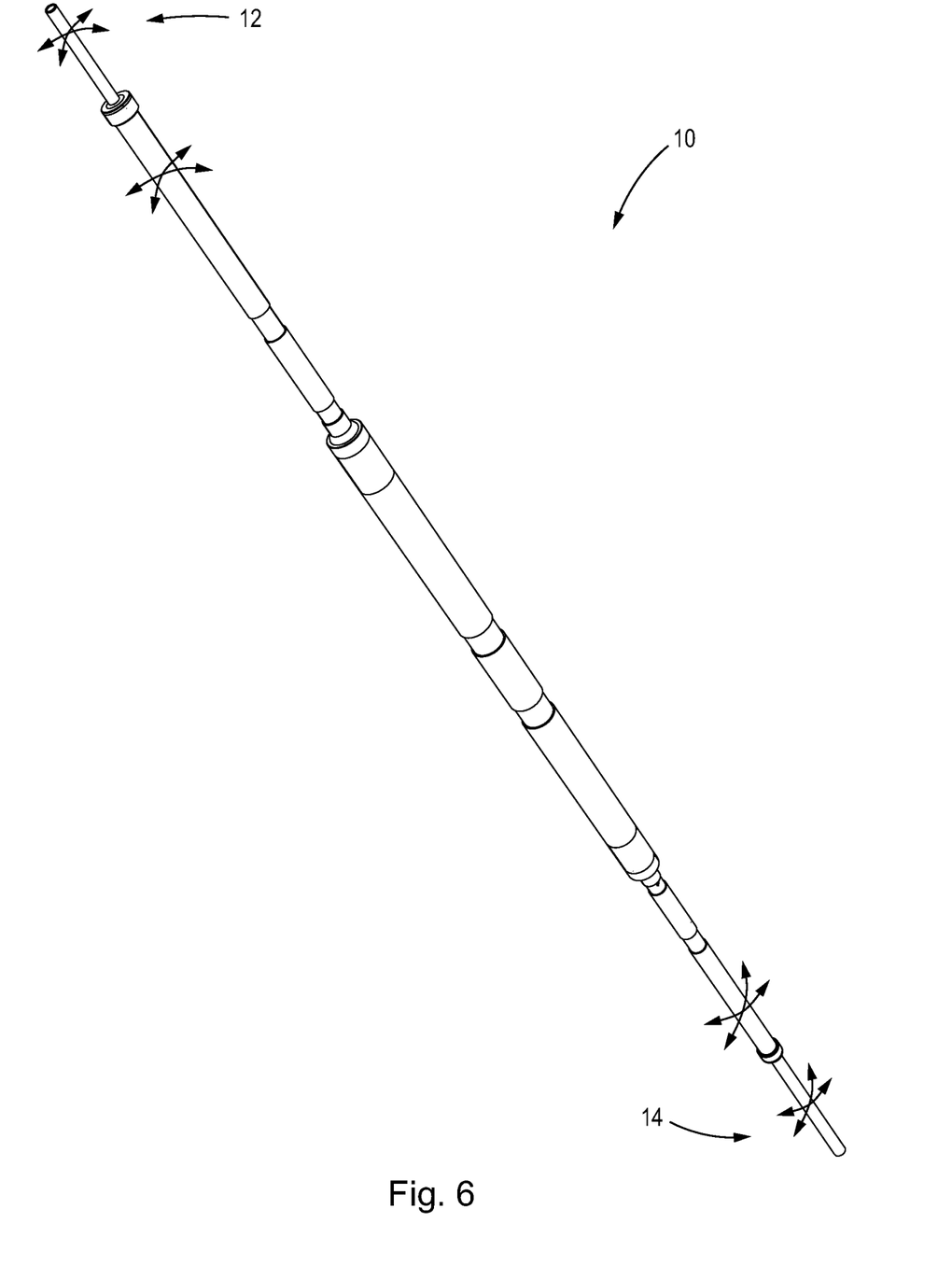
FIG. 6 shows a second embodiment of an endoscopic instrument.

FIG. 6 shows a second embodiment of an endoscopic instrument 10 with a proximal end 12 and a distal end 14.

Figure 7:
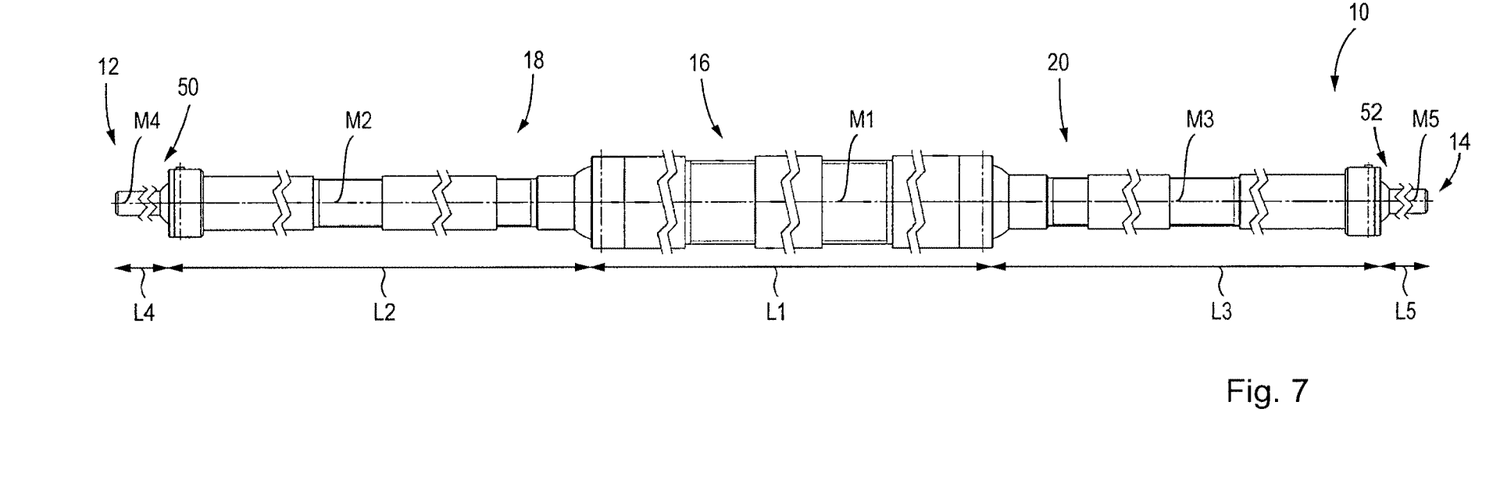
FIG. 7 shows a side view of the endoscopic instrument according to FIG. 6.

FIG. 7 shows a side view of the endoscopic instrument 10 according to FIG. 6. All the explanations which were given in conjunction with FIG. 2 apply. In addition, the instrument 10 has a fourth portion 50 with a fourth longitudinal extent L4 and a fourth center axis M4 and a fifth portion 52 with a fifth longitudinal extent L5 and a fifth center axis M5.

Figure 8:
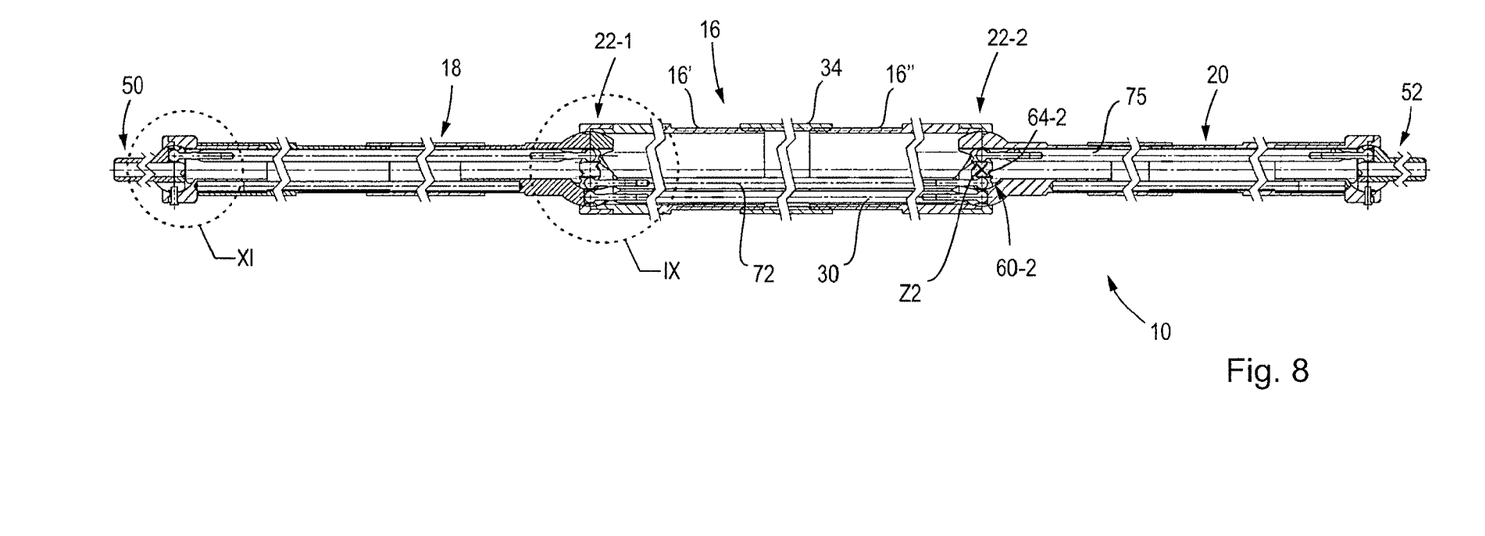
FIG. 8 shows a sectional view of the endoscopic instrument according to FIG. 6.

FIG. 8 shows a sectional illustration of the endoscopic instrument 10 according to FIG. 7. All that has been said in relation to FIG. 3 applies. The differences between the second embodiment shown here and the first embodiment will be explained hereinbelow.

Figure 9:
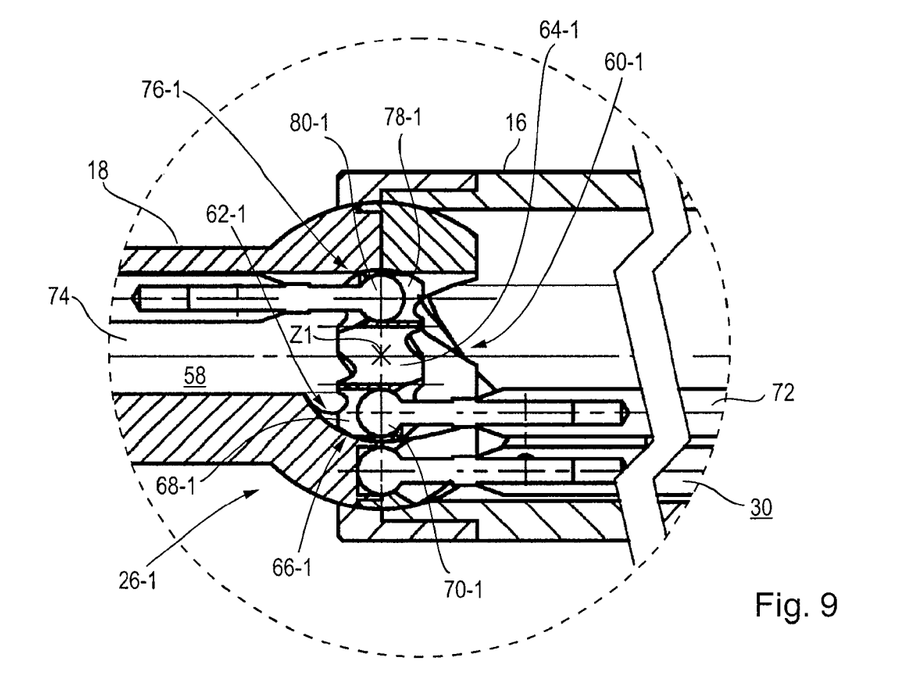
FIG. 9 shows an enlargement of a detail from FIG. 8.

FIG. 9 shows an enlargement of a detail from FIG. 8. All the explanations which were given in relation to FIG. 4 apply. The further first main-hinge part 26-1 has a first inner hinge 60-1, which is arranged in the interior of the further first main-hinge part 26-1 and is arranged such that it can be pivoted relative to the further first main-hinge part 26-1. The second portion 18 has a second cavity 58 along the second longitudinal extent L2.

The first inner hinge 60-1 has a first inner-hinge part 62-1 and a further first inner-hinge part 64-1. The first inner-hinge part 62-1 is designed at least in the form of a portion of a socket. The further first inner-hinge part 64-1 is designed at least in the form of a portion of a ball. The first inner-hinge part 62-1 is formed on the further first main-hinge part 26-1. In other words, the inner surface of the further first main-hinge part 26-1 is designed such that the further first inner-hinge part 64-1 can shift in the further first main-hinge part 26-1 in the same way as in a socket.

The further first inner-hinge part 64-1 has a first primary hinge 66-1 with a first primary-hinge part 68-1 and a further first primary-hinge part 70-1. The first primary-hinge part 68-1 is formed on the further first inner-hinge part 64-1, in this case in the form of a portion of a socket, of which only part can be seen in the sectional illustration. The endoscopic instrument also has a rigid secondary pressure rod 72, which extends along the first longitudinal extent L1, wherein the further first primary-hinge part 70-1 is formed on the secondary pressure rod 72. The first primary hinge 66-1 is designed such that the secondary pressure rod 72 can subject the further first inner-hinge part 64-1 both to a positive pressure and to a negative pressure.

The instrument 10 also has a first rigid lateral pressure rod 74, which extends along the second longitudinal extent L2. The further first inner-hinge part 64-1 also has a first secondary hinge 76-1 with a first secondary-hinge part 78-1 and a further first secondary-hinge part 80-1. The first secondary-hinge part 78-1 is formed on the further first inner-hinge part 64-1, and the further first secondary-hinge part 80-1 is formed on the first lateral pressure rod 74.

All the explanations which are given in relation to FIG. 9 also apply correspondingly to the second inner hinge 60-2.

In order to clarify the functioning, two exemplary possible applications will be explained with reference to FIGS. 8 and 9. In the first instance, the first lateral pressure rod 74 can be displaced to the right, as seen in relation to the orientation in the drawing. The further first inner-hinge part 64-1 thus rotates in the clockwise direction about the first center point Z1. As a result, the first primary hinge 66-1 is likewise displaced about the first center point Z1 and displaces the secondary pressure rod 72 to the left. The secondary pressure rod 72, which is also coupled to the second further inner-hinge part 64-2, displaces the further second inner-hinge part 64-2 in the clockwise direction about the second center point Z2. The second lateral pressure rod 75 is thus displaced to the right.

In the second case, the second portion 18 is angled in the clockwise direction about the first center point Z1. This angling pulls the main pressure rod 30 to the left. Since the main pressure rod 30 is coupled to the further second main-hinge part 26-2, the third portion 20 is displaced in the clockwise direction about the second center point Z2.

Figure 10:
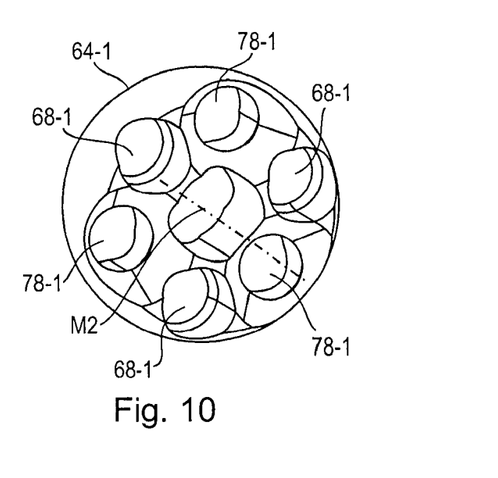
FIG. 10 shows a simplified illustration of a plan view of the further first inner-hinge part.

FIG. 10 shows a perspective illustration of the further first inner-hinge part 64-1. It can be seen that the first primary-hinge parts 68-1 and the first secondary-hinge parts 78-1 are arranged in alternating fashion in the manner of a ring around the second center axis M2. Upon actuation of the instrument 10, in each case a first primary-hinge part 68-1 and a first secondary-hinge part 78-1, located diametrically opposite, belong functionally together. The proposed embodiment of the further first inner-hinge part 64-1 is referred to as a socket ring.

Figure 11:
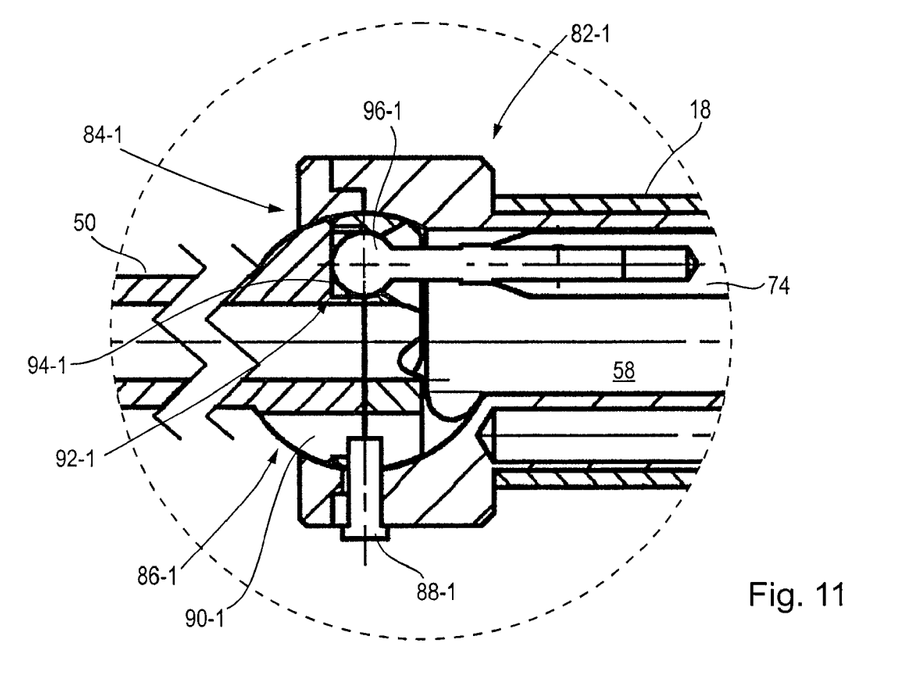
FIG. 11 shows a further enlargement of a detail from FIG. 8.

FIG. 11 shows a further enlargement of a detail from FIG. 8. It shows a first lateral hinge 82-1, which has a first lateral-hinge part 84-1 and a further first lateral-hinge part 86-1. A first guide pin 88-1 engages in a first hinge groove 90-1 and prevents the fourth portion 50 from rotating about the fourth center axis M4.

The further first lateral-hinge part 86-1 also has a first lateral sub-hinge 92-1, which is formed from a first lateral sub-hinge part 94-1 and a further first lateral sub-hinge part 96-1. The first lateral sub-hinge part 94-1 is designed at least in the form of a portion of a socket, and the further first lateral sub-hinge part 96-1 is designed at least in the form of a portion of a ball. The further first lateral sub-hinge part 96-1 is formed on the first lateral pressure rod 74. Angling of the fourth portion 50 thus results in displacement of the first lateral pressure rod 74.

As a result, this construction makes it possible, inter alia, for angling of the fourth portion 50 to give rise to angling of the fifth portion 52 and for angling of the second portion 18 to give rise to angling of the third portion 20. Since the aforementioned pressure rods are rigid, positive and negative compressive forces can be transmitted in a particularly reliable manner.

What is claimed is:

1. An endoscopic instrument, comprising:
   a first shaft;
   a second shaft pivotably connected to a proximal end of the first shaft via a proximal main hinge having a socket part and a ball part;
   a third shaft pivotably connected to a distal end of the first shaft via a distal main hinge having a socket part and a ball part;
   a main pressure rod coupled between the ball part of the proximal main hinge and the ball part of the distal main hinge, such that displacement of the proximal main hinge by angling the second shaft relative to the first shaft transmits a force, via the main pressure rod, to the distal main hinge and causes there an angling of the third shaft relative to the first shaft;

a fourth shaft pivotably connected to a proximal end of the second shaft via a proximal lateral hinge having a socket part and a ball part;

a fifth shaft pivotably connected to a distal end of the third shaft via a distal lateral hinge having a socket part and a ball part;

a proximal inner hinge arranged in an interior of the ball part of the proximal main hinge, the proximal inner hinge pivotable relative to the ball part of the proximal main hinge;

a distal inner hinge arranged in an interior of the ball part of the distal main hinge, the distal inner hinge pivotable relative to the ball part of the distal main hinge;

a proximal lateral pressure rod coupled between the proximal inner hinge and the proximal lateral hinge;

a secondary pressure rod coupled between the proximal inner hinge and the distal inner hinge;

a distal lateral pressure rod coupled between the distal inner hinge and the distal lateral hinge;

wherein displacement of the proximal lateral hinge by angling the fourth shaft relative to the second shaft transmits a force to the proximal inner hinge via the proximal lateral pressure rod, which in turn transmits the force to the distal inner hinge via the secondary pressure rod, which in turn transmits the force to the distal lateral hinge via the distal lateral pressure rod, which thereby causes there an angling of the fifth shaft relative to the third shaft.

2. The endoscopic instrument of claim 1, wherein the secondary pressure rod is a first secondary pressure rod;

wherein the endoscopic instrument further comprises a second secondary pressure rod and a third secondary pressure rod, each coupled between the proximal inner hinge and the distal inner hinge;

wherein the first, the second, and the third secondary pressure rods are circumferentially spaced apart by 120 degrees relative to a center axis of the first shaft.

3. The endoscopic instrument of claim 2, wherein the proximal lateral pressure rod is a first proximal lateral pressure rod;

wherein the endoscopic instrument further comprises a second proximal lateral pressure rod and a third proximal lateral pressure rod, each coupled between the proximal inner hinge and the proximal lateral hinge; and wherein the first, the second, and the third proximal lateral pressure rods are circumferentially spaced apart relative to a center axis of the second shaft.

4. The endoscopic instrument of claim 3, wherein the distal lateral pressure rod is a first distal lateral pressure rod;

wherein the endoscopic instrument further comprises a second distal lateral pressure rod and a third distal lateral pressure rod, each coupled between the distal inner hinge and the distal lateral hinge; and wherein the first, the second, and the third distal lateral pressure rods are circumferentially spaced apart relative to a center axis of the third shaft.

5. The endoscopic instrument of claim 1, wherein the socket part of the proximal main hinge is formed on the proximal end of the first shaft; and wherein the socket part of the distal main hinge is formed on the distal end of the first shaft.

6. The endoscopic instrument of claim 5, wherein the ball part of the proximal main hinge is formed on a distal end of the second shaft; and wherein the ball part of the distal main hinge is formed on a proximal end of the third shaft.

7. The endoscopic instrument of claim 1, wherein the ball part of the proximal main hinge includes a socket sub-part that receives a ball part on a proximal end of the main pressure rod; and wherein the ball part of the distal main hinge includes a socket sub-part that receives a ball part on a distal end of the main pressure rod.

8. The endoscopic instrument of claim 1 wherein the main pressure rod is a first main pressure rod;

wherein the endoscopic instrument further comprises a second main pressure rod and a third main pressure rod each coupled between the ball part of the proximal main hinge and the ball part of the distal main hinge; and wherein the first, the second, and the third main pressure rods are circumferentially spaced apart relative to a center axis of the first shaft.

9. The endoscopic instrument of claim 1, wherein the main pressure rod and the secondary pressure rod are displaceable relative to one another.

10. The endoscopic instrument of claim 1, wherein the main pressure rod and the secondary pressure rod extend parallel relative to one another.

11. The endoscopic instrument of claim 1, wherein the first shaft is divided into a first part and a second part, and the first part and the second part are connected by a connecting element such that adjusting a distance between the first part and the second part is possible.

12. The endoscopic instrument of claim 1, wherein the proximal inner hinge includes a ball part and a socket part; and wherein the socket part of the proximal inner hinge is formed on the ball part of the proximal main hinge; and wherein the ball part of the proximal inner hinge is disposed within the ball part of the proximal main hinge.

13. The endoscopic instrument of claim 12, wherein the distal inner hinge includes a ball part and a socket part; and wherein the socket part of the distal inner hinge is formed on the ball part of the distal main hinge; and wherein the ball part of the distal inner hinge is disposed within the ball part of the distal main hinge.

14. The endoscopic instrument of claim 13, wherein the ball part of the proximal inner hinge includes a first socket sub-part that receives a ball part on a proximal end of the secondary pressure rod; and wherein the ball part of the distal inner hinge includes a first socket sub-part that receives a ball part on a distal end of the secondary pressure rod.

15. The endoscopic instrument of claim 14, wherein the ball part of the proximal inner hinge includes a second socket sub-part that receives a ball part on a distal end of the proximal lateral pressure rod; and wherein the ball part of the distal inner hinge includes a second socket sub-part that receives a ball part on a proximal end of the distal lateral pressure rod.

* * * * *